US00PP08174P

United States Patent [19]

Schumann

[11] Patent Number: Plant 8,174

[45] Date of Patent: Mar. 9, 1993

[54] GERANIUM PLANT NAMED FISHOG

[75] Inventor: Ingeborg Schumann, Münster, Fed. Rep. of Germany

[73] Assignee: Florfis AG, Binningen, Switzerland

[21] Appl. No.: 779,298

[22] Filed: Oct. 18, 1991

[51] Int. Cl.[5] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of Geranium named Fishog, particularly characterized by the combined features of light salmon pink flower color, semi-double flower form, medium green foliage with strong zonation, and vigorous growth.

1 Drawing Sheet

The present invention comprises a new and distinct cultivar of Geranium, botanically known as *Pelargonium zonale L'Hert,* and hereinafter referred to by the cultivar name Fishog.

Fishog is a product of planned breeding program which had the objective of creating new Geranium cultivars with light salmon pink flower color, semi-double flower form and comparatively vigorous growth.

Fishog is an inbred seedling and was originated from a hybridization made by the inventor Ingeborg Schumann in a controlled breeding program in Galdar, Gran Canaria, Spain in 1986. Fishog was derived from an unnamed seedling that was obtained by crossing a female hybrid resulting from a cross between Erfolg and Achspen (also known by the trademark "Lachsball"), with the male parent Summer Cloud. Variety Erfolg is characterized by pink semi-double flowers and medium green leaves with strong zonation. Achspen has salmon (white-orange marbled) flowers and leaves without zonation. Summer Cloud is characterized by white semi-double flowers, vigorous growth, and leaves with strong zonation.

Fishog was discovered and selected as one flowering plant within the progeny of the stated cross by Ingeborg Schumann in spring 1987 in a controlled environment in Galdar, Gran Canaria, Spain.

The first act of asexual reproduction of Fishog was accomplished when vegetative cuttings were taken from the initial selection in February 1988 in a controlled environment in Hillscheid, Federal Republic of Germany by, or under the supervision of, Ingeborg Schumann.

Horticultural examination of selected units initiated in May 1988 and continuing thereafter has demonstrated that the combination of characteristics as herein disclosed for Fishog are firmly fixed and are retained through successive generations of asexual reproduction.

Fishog has not been observed under all possible environmental conditions. The phenotype may vary somewhat with variations in environment such as temperature, light intensity and day length, without, however, any variance in the genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fishog, which in combination distinguish this Geranium as a new and distinct cultivar:

1. Light salmon flowers with white margin
2. Semi-double flower form
3. Medium green foliage with strong zonation
4. Vigorous growth
5. Good branching characteristics Of the many commercial cultivars known to the present inventor, the most similar in comparison to Fishog is the cultivar identified by the trademark "Champagne" (cultivar name is Fischa). Reference is made to attached Chart A which compares certain characteristics of Fishog to those same characteristics of Champagne. In general comparison to Champagne, Fishog has a semi-double flower and much better resistance to shattering. Fishog also has a more vigorous growth and a later spring flower response.

The accompanying color photographic drawing is a top perspective view showing typical flower and foliage characteristics of Fishog, with colors being as true as possible with illustrations of this type.

In the following description color references are made to the Royal Horticultural Society Colour Chart. The color values were determined indoors from flowers taken from plants grown outdoors in June at Hillscheid, Federal Republic of Germany.

Classification:

*Botanical.*—A hybrid of the species *Pelargonium zonale L'Hert.*

*Commercial.*—Zonal Geranium, cv. Fishog.

INFLORESCENCE

A. Umbel:

*Average diameter.*—104 mm.

*Average depth.*—65 mm.

*Peduncle length.*—150 mm.

*Pedicel length.*—26 mm.

*Number of flowers per umbel.*—About 30–40.

B. Corolla:

*Average diameter.*—46 mm.

*Form.*—Semi-double.

*Number of petals.*—5–7.

*Color (general tonality from a distance of three meters).*—Light salmon.

*Color of top surface, near center.*—R.H.S. 52C-D.

*Color of top surface, near margin.*—R.H.S. 56D or white.

*Color of lower side.*—White to light salmon, marbled: R.H.S. 52D and lighter.

C. Bud:

*Shape.*—Round, pointed.

*Color (sepals).*—Light green.

*Color (tips of petals).*—White and pink marbled.

D. Reproductive organs:

*Androecium.*—5–8 stamens, 5 fertile at minimum, with orange pollen.

*Gynoecium.*—5–6 lobed stigma, red.

E. Spring flowering response period: In Hillscheid, Federal Republic of Germany, in 1989 60% of plants with at least 1 flower opened 12 weeks after planting of unrooted cuttings.

F. Outdoor flower production: The flower count in 1898 in Hillscheid, Federal Republic of Germany indicated between 45 and 50 flowers per plant for May through September observation period.

G. Durability: Shatter resistance comparatively good. Rain resistance medium to good.

PLANT

A. Foliage:

*Form.*—Round to kidney shaped, closed at the base.

*Margin.*—Bicrenated.

*Color (upper surface).*—Medium green, about R.H.S. 137C.

*Color (zonation).*—Reddish brown, about R.H.S. 176A, forming a broad ring.

*Tolerance of botrytis.*—Medium.

B. General appearance and form:

*Internode length.*—1–2 cm.

*Branching pattern.*—6.2 branches after 13 weeks of growing time.

*Height.*—32 cm in August.

CHART A

| | FISHOG | CHAMPAGNE |
|---|---|---|
| White margin of flowers | marked white margin, the width ranging from ⅛ to ⅓ of the petals | diffuse pale salmon margin |
| Flower form | 6–7 petals | 5 petals |
| Growth | vigorous | medium |
| Plant habit | large, broad | medium-large |
| Height (of foliage) | 32 cm | 25 cm |
| Beginning of flowering (% of flowering plants in 12th week) | 60% | 75% |
| Shattering of petals | medium | strong |

I claim:

1. A new and distinct cultivar of Geranium plant named Fishog, as illustrated and described.

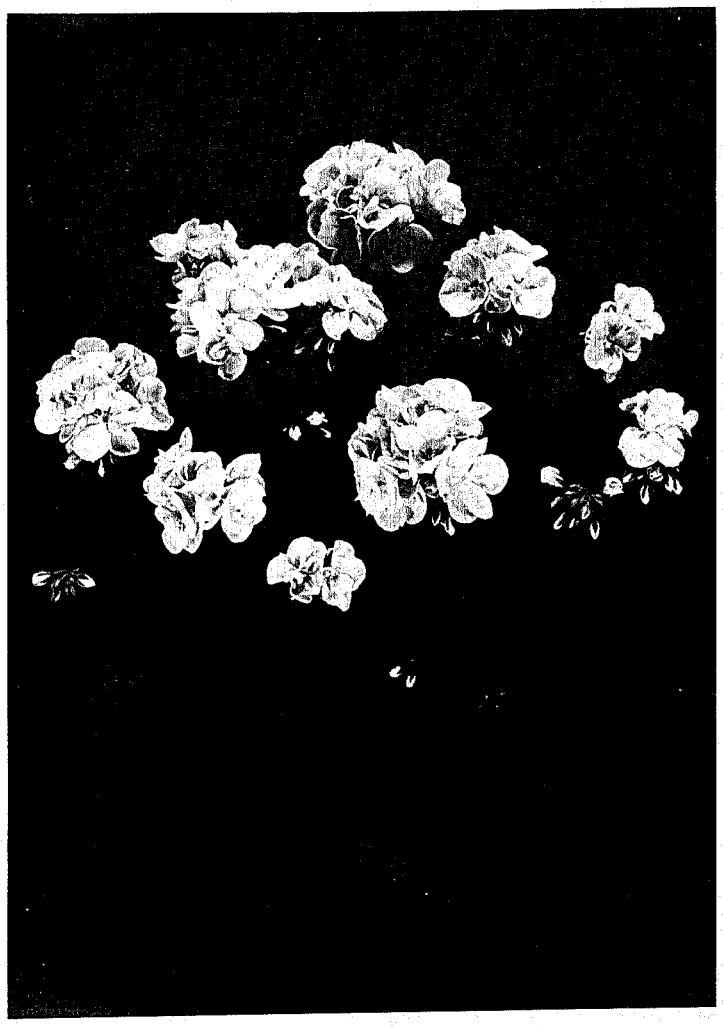

* * * * *